United States Patent
Keipert et al.

[11] Patent Number: 5,553,629
[45] Date of Patent: Sep. 10, 1996

[54] PORTABLE MEDICAL LASER PACK SYSTEM

[75] Inventors: Andreas G. Keipert; Michael S. Allen, both of Albuquerque, N.M.

[73] Assignee: The United States of America as represented by the Secretary of the Air Force, Washington, D.C.

[21] Appl. No.: 31,257

[22] Filed: Mar. 11, 1993

[51] Int. Cl.$^6$ ................................. A61B 17/36
[52] U.S. Cl. ................. 128/898; 606/13; 606/16; 372/109
[58] Field of Search ................. 606/2, 10–18, 606/3; 128/395–398, 898; 372/43, 44, 75, 6, 34, 45, 109; 385/45, 31, 39, 49, 88, 89, 901, 902; 219/121.6, 121.67, 121.76

[56] References Cited

U.S. PATENT DOCUMENTS

| | | | |
|---|---|---|---|
| 4,713,821 | 12/1987 | Bradford et al. | 372/44 |
| 4,808,789 | 2/1989 | Muncheryan | 219/121.6 |
| 4,826,431 | 5/1989 | Fujimura et al. | 606/14 |
| 4,905,690 | 3/1990 | Ohshiro et al. | 128/395 |
| 5,026,366 | 6/1991 | Leckrone | 606/15 |
| 5,056,097 | 10/1991 | Meyers | 372/109 |
| 5,074,861 | 12/1991 | Schneider et al. | 606/17 |
| 5,147,349 | 9/1992 | Johnson et al. | 606/4 |
| 5,195,155 | 3/1993 | Shimaoka et al. | 385/90 |
| 5,272,716 | 12/1993 | Soltz et al. | 372/6 |

*Primary Examiner*—Angela D. Sykes
*Assistant Examiner*—Michael Peffley
*Attorney, Agent, or Firm*—Robert L. Nathans

[57] ABSTRACT

A fiber optic cable has one end directly coupled to a semiconductor IR generating laser diode array and the other end is used to direct IR radiation at a soldier's wound for surgical purposes. The beam may also be used to illuminate a dark scene to detect the presence of a present threat such as a sniper. The components are conveniently carried by the medically trained person in his belt pack so as not to interfere with his freedom of movement. Disposable IR applicator tips may also be provided to be attached to the IR exit portion of the fiber optic cable.

6 Claims, 1 Drawing Sheet

PORTABLE MEDICAL LASER PACK SYSTEM

STATEMENT OF GOVERNMENT INTEREST

The invention described herein may be manufactured and used by or for the Government for governmental purposes without the payment of any royalty thereon.

BACKGROUND OF THE INVENTION

The present invention relates to the field of surgical use of lasers.

Compact, portable, surgical devices which employ a diode laser optically coupled to one end of a fiber optic cable which in turn directs IR upon the retina of a patient via a light applicator tip member mounted upon the other end of the cable are known in the art. See U.S. Pat. No. 5,147,349 issued to Johnson et al. This patent also teaches employing a visible aiming beam merged with the invisible IR beam to aid the surgeon in positioning the IR beam. The electronic control system described in detail in the patent, enables the operator to deliver a continuous beam, a series of pulses or a single pulse. The operator also may select the power level which ranges between 0.1 and one watt. However, we desire to provide power levels between five and twenty-five watts to perform general surgical cutting, closing and coagulating of wounds in the field.

It is deemed desirable to provide a highly practical high power portable surgical laser instrument for military field paramedics and physicians. It is also desirable to provide such a device which is completely self-contained, is lightweight and is carried by medically trained personnel in a manner to minimize any adverse impact on his or her effectiveness in the field.

There is also a need to covertly render a night scene immediately visible to the personnel carrying the device in order to spot a dangerous situation such as the presence of a sniper or to aid in locating the wounded. It would also be beneficial to provide such a laser instrument, which will be useful for civilian paramedics as well, who may be called by the police to render medical attention to wounded persons.

BRIEF SUMMARY OF THE INVENTION

In accordance with the present invention, a portable, lightweight, medical device is provided which includes a semiconductor laser diode array for generating infra-red radiation, a power source, a fiber optic cable having a first terminal portion optically coupled to the semiconductor diodes of the laser diode array and having a second terminal portion for applying the infra-red (IR) radiation to the body of a person for surgical purposes. The medically trained carrier of the device is also provided with a viewing device such as IR goggles, for making a scene illuminated by infra-red radiation generated by the same device visible, so that a dark scene may be viewed by directing the infra-red beam at the scene in order to detect a dangerous situation such as the presence of a sniper. The diode array comprises several diodes to provide the high power desired for these two functions.

BRIEF DESCRIPTION OF THE DRAWINGS

Other features and advantages will become apparent upon study of the following description taken in conjunction with the drawings in which.

DETAILED DESCRIPTION OF PREFERRED EMBODIMENTS OF THE INVENTION

Figure 1:
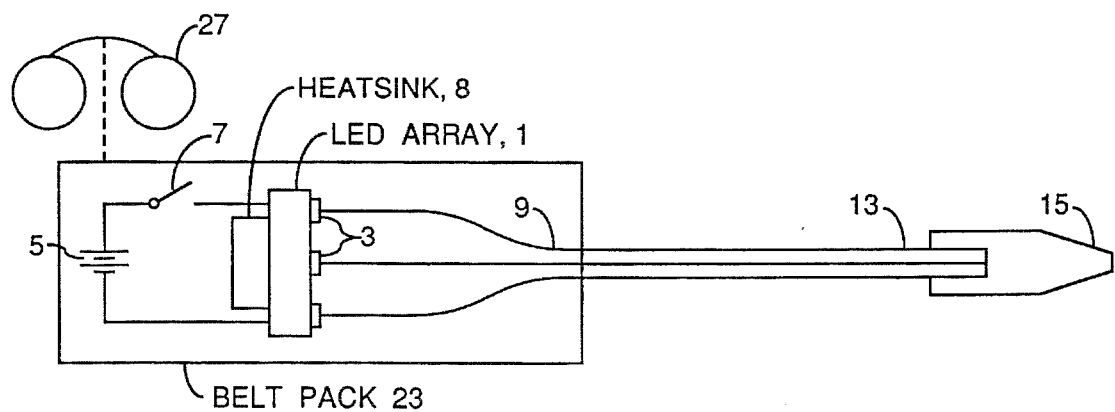
FIG. 1 illustrates a preferred embodiment of the invention.

Referring now to FIG. 1, a semiconductor laser diode array 1, comprising at least several infra-red (IR) generating semiconductor diodes 3, is energized by power source 5 upon the closing of switch 7. Fiber optic cable 11 has a first terminal portion 9 directly abutting diodes 3 via a pig-tailed fiber configuration, while a second opposite terminal portion 13 is fitted within an optional disposable IR tip applicator 15.

High power diode lasers are now known in the art and can generate substantial power in the near IR wavelength bands. Their efficiencies can be 25-40%. These lasers have small sizes, are reliable, have long life and do not require cumbersome high voltage sources. Operation around 800 nm is typical. Our working prototype used a pair of two volt batteries to power the diode array. At the second terminal portion 13 of the cable, the IR light beams produced by the array 1, are very intense and thus the beams are highly effective for surgical purposes, that is, for cutting and coagulating wounds in the field. Tests have shown us that five to ten watts operating in the near IR can produce adequate surgical results, typically in five to fifteen second exposures.

The commercially available disposable tip applicator 15 can be fitted over the fiber optic terminal portion 13. This member is readily removable to provide for the use of various types of disposable and sterile medical contact IR tip applicators that are suited to different wound treating medical procedures such as cutting, coagulation and closing operations. For example, conical tip applicators are more suited to cutting operations, whereas orb tip applicators are more suitable for cauterizing.

Selection of particular semiconductor laser diodes will depend upon the exact type of surgery desired, and such selection is well within the skill of the ordinary worker in the art. Single linear, incoherent arrays 1 directly coupled into the fiber optic cable 11, can provide powers ranging from five to twenty-five watts. The use of multiple diode arrays enables the production of elevated power from the arrays and redundancy benefits are also produced due to diode duplication. Reliability is of great importance in this environment. We can focus to very small spots providing very bright intensities when coupled to high temperature resistant tip members 15 such as quartz or sapphire. Suitable laser diodes offering a conversion efficiency of 25 %, and which can operate in the near IR band, and laser diode arrays of such diodes are described in U.S. Pat. No. 4,808,789 to Muncheryan.

A heatsink 8 may also be provided to help dissipate the heat produced by the laser diode array. Phase change material heatsinks were successfully tested. The heatsink will absorb the heat to be dissipated over several times the required run time of the device, which should be in the neighborhood of at least several minutes. Borax material ($NABO_2$-$4H_2O$) which melts at 57 degrees C., provides good energy absorbing capacity over a large range of ambient temperatures, which is also important for this application. An optional thermo-electric (TE) heat pump can be used to heat the phase change material to its melting point. However, anticipated upgrades will probably use a newly available InGaAs laser that has a higher operating temperature of greater than 50 degrees C which will simplify the design so that the optional TE heat pump will be omitted. Also, for power source 5, nickel-cadmium batteries looked most promising due to their high current discharge and low voltage requirements.

The aforesaid components, can be readily fitted within belt pack 23, so that the device is highly portable and importantly, may be carried by the medically trained personnel to minimize adverse impact on the movements of the person and hence their effectiveness under trying field conditions. The belt pack, mounted upon the belt of the operator, has typical dimensions of about 3×3×7 inches.

The device has a second dual use of great importance. The wounded being treated may have been shot or otherwise attacked by a close-by enemy. To check on whether there is present danger, the divergent IR exiting the fiber illuminates the area if the operation is being carried out in the dark. The operator now utilizes an IR viewing device such as a pair of IR goggles 27 or an IR image intensifier to look for a possible present threat. The IR goggles would be carried by the medical personnel as schematically indicated in FIG. 1. Thus, the IR wavelength is advantageously employed for both surgery and night surveillance. Although the device is compact and highly portable, the high power levels used for medical purposes, can brightly illuminate substantial portions of a dark landscape. This IR light which is invisible to the naked eye can aid in covertly searching for the wounded as well.

Figure 2:
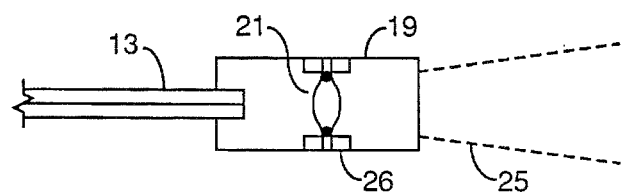
FIG. 2 schematically illustrates an optional optical lens means for adjusting the illumination degree of divergence of infra-red radiation produced by the device.

Since the angle of divergence of the IR radiation exiting the disposable tip 15 is substantial, it often illuminates the area in a satisfactory manner. Thus the disposable tip member also functions as a search light member. However, if a greater degree of flexibility is desired, the degree of divergence of the IR beam exiting the device may be adjusted by a simple adjustable optical search light member arrangement comprising a single movable lens illustrated in FIG. 2. A housing 19 could be fitted over the end of the cable as shown in FIG. 2 after the removal of the disposable tip 15, such housing containing a movable lens 21, mounted within a conventional threaded lens barrel schematically indicated at 26. Rotation of the lens barrel will translate the lens relative to the housing to change the degree of divergence of the IR beam from a highly divergent beam 25 to a less divergent beam. This would illuminate smaller areas with IR beams of greater intensity.

Various embodiments of the invention, other than those specifically described, will be readily apparent to those skilled in the art, and thus the scope of the invention is to be limited only by the terms of the following claims and art recognized equivalents thereof. For example, while the embodiment of the invention described above employs optical fibers directly coupled to the laser diodes, we have also worked with lasers where very small lenses are used to couple the laser energy into the fiber which allows for higher coupling efficiencies. Also, individual fiber coupled lasers may be employed in place of the array illustrated herein.

We claim:

1. A method of employing a medical laser device comprising the steps of:
    (a) providing said medical device which includes a semiconductor laser diode means for generating infra-red radiation;
    (a-1) a power source for energizing said semiconductor laser diode means; and
    (a-2) a fiber optic cable having a first terminal portion optically coupled to the semiconductor laser diode means and having a second terminal portion for applying said infra-red radiation to the body of a person for surgical purposes;
    (b) providing medically trained personnel carrying said medical laser device with a viewing device for making a scene illuminated by infra-red radiation visible;
    (c) directing infra-red radiation exiting the second terminal portion of said fiber optic cable at the nearby body of a person for surgical purposes; and
    (d) alternatively, directing infra-red radiation exiting the second terminal portion of said fiber optic cable at a scene for viewing the scene with the aid of said viewing device.

2. The method of claim 1 including the step of transporting the medical laser device in a belt pack adapted to be carried by a medically trained person.

3. The method of claim 1 including the step of causing the infra-red radiation to widely diverge as it exits from the second terminal portion of the fiber optic cable, thereby to produce an infra-red searchlight.

4. A method of employing a medical laser device comprising the steps of:
    (a) providing said medical device which includes an infra-red light source; and
    (a-1) a power source for energizing said infra-red light source; and
    (a-2) a fiber optic cable having a first terminal portion optically coupled to the infra-red light source and having a second terminal portion for applying said infra-red radiation to the body of a person for surgical purposes;
    (b) providing medically trained personnel carrying said medical laser device with a viewing device for making a scene illuminated by infra-red radiation visible;
    (c) directing infra-red radiation exiting the second terminal portion of said fiber optic cable at the nearby body of a person for surgical purposes; and
    (d) alternatively, directing infra-red radiation exiting the second terminal portion of said fiber optic cable at a scene for viewing the scene with the aid of said viewing device.

5. The method of claim 4 including the step of transporting the medical laser device in a belt pack adapted to be carried by a medically trained person.

6. A method of employing a medical laser device comprising the steps of:
    (a) providing said medical device which includes an infra-red light source; and
    (a-1) a power source for energizing said infra-red light source;
    (b) providing medically trained personnel carrying said medical laser device with a viewing device for making a scene illuminated by infra-red radiation visible;
    (c) directing infra-red radiation from said infra-red light source at the nearby body of a person for surgical purposes; and
    (d) alternatively, directing a broad beam of infra-red radiation produced by said infra-red light source at a scene for viewing the scene with the aid of said viewing device.

* * * * *